United States Patent
Hirai et al.

(12) 
(10) Patent No.: US 6,710,038 B1
(45) Date of Patent: Mar. 23, 2004

(54) EMULSIFICATION METHOD USING PROPYLENE GLYCOL HYALURONATE

(75) Inventors: Hideki Hirai, Tokyo (JP); Michiki Asai, Tokyo (JP)

(73) Assignee: Kibun Food Chemifa Co., Ltd., Tokyo (JP)

( * ) Notice: Subject to any disclaimer, the term of this patent is extended or adjusted under 35 U.S.C. 154(b) by 0 days.

(21) Appl. No.: 09/607,929

(22) Filed: Jun. 30, 2000

(30) Foreign Application Priority Data

Dec. 14, 1999 (JP) .......................................... 11/355160

(51) Int. Cl.⁷ ........................ A61K 31/715; A61K 7/00; A61K 9/14; A01N 25/00; C08B 37/00; A61F 2/00; A61F 13/00

(52) U.S. Cl. ........................ 514/54; 514/844; 514/880; 536/55.1; 424/401; 424/423; 424/443; 424/489

(58) Field of Search ................. 424/401, 423, 424/489, 443; 536/55.1; 514/54, 844, 880

(56) References Cited

U.S. PATENT DOCUMENTS

| | | | |
|---|---|---|---|
| 4,784,990 A | * 11/1988 | Nimrod et al. | ............... 514/54 |
| 4,851,521 A | 7/1989 | Della Valle et al. | |
| 4,957,744 A | 9/1990 | Della Valle et al. | |
| 4,965,353 A | 10/1990 | Della Valle et al. | |
| 5,166,331 A | 11/1992 | Della Valle et al. | |
| 5,202,431 A | 4/1993 | Della Valle et al. | |
| 5,336,767 A | 8/1994 | Della Valle et al. | |
| 5,569,767 A | * 10/1996 | Uphues et al. | ............ 548/352.1 |
| 6,107,347 A | * 8/2000 | Francese et al. | ............ 514/772 |
| 6,200,595 B1 | * 3/2001 | Motoyashiki et al. | ....... 424/445 |

FOREIGN PATENT DOCUMENTS

| | | |
|---|---|---|
| EP | 0 216 453 | 4/1987 |
| EP | 0 265 116 | 4/1988 |
| JP | 51-86117 | 7/1976 |
| JP | 52-143218 | 11/1977 |
| JP | 52-151718 | 12/1977 |
| JP | 58-49311 A | 3/1983 |
| JP | 58-183938 A | 10/1983 |
| JP | 58-201711 A | 11/1983 |
| JP | 61-27966 A | 2/1986 |
| JP | 62-500102 | 1/1987 |
| JP | 62-501631 A | 7/1987 |
| JP | 63-208536 A | 8/1988 |
| JP | 63-208537 A | 8/1988 |
| JP | 3-143540 A | 6/1991 |
| JP | 7-108166 A | 4/1995 |
| JP | 7-55961 B2 | 6/1995 |
| JP | 9-157129 A | 6/1997 |
| JP | 2001-278981 A | 10/2001 |
| JP | 2001-288233 A | 10/2001 |
| WO | WO 86/01103 | 2/1986 |
| WO | WO 86/03938 A1 | 7/1986 |

OTHER PUBLICATIONS

Translation of JP 06–298804, 1994.
Patent Abstracts of Japan; vol. 015, No. 361 (C–0867), Sep. 12, 1991; & JP 03143540A (Agency of Ind. Science & Technol. others: 01), Jun. 19, 1991.
Patent Abstracts of Japan; vol. 1995, No. 01, Feb. 28, 1995; & JP 06 298804 A (Shiseido Co. Ltd.), Oct. 25, 1994.

* cited by examiner

Primary Examiner—Shengjun Wang
(74) Attorney, Agent, or Firm—Browdy and Neimark, P.L.L.C.

(57) ABSTRACT

Disclosed are propylene glycol hyaluronate esters having an esterification degree of 10–90% and a limiting viscosity of 3-35 dL/g as well as skin conditioning methods, moisturizing methods and emulsifying methods using said propylene glycol hyaluronate esters. Propylene glycol hyaluronate esters of the present invention are compounds showing excellent viscosity stability in low-pH systems and cation-containing systems and also showing high emulsifiability, hydration power and moisturizing effect.

17 Claims, No Drawings

EMULSIFICATION METHOD USING PROPYLENE GLYCOL HYALURONATE

FIELD OF THE INVENTION

The present invention relates to propylene glycol hyaluronate esters and agent for external use to skin, which refers to "skin preparations for external use" hereinafter, containing said propylene glycol hyaluronate esters. Skin preparations for external use according to the present invention can be widely used as cosmetic and pharmaceutical products because of their excellent viscosity stability, emulsifiability, hydration power and moisturizing effect.

RELATED ART

Dry skin is caused by excessive loss of moisture from the surface of the skin exposed to dry air or cleansing. In these days, various environmental chemical substances also inhibit skin functions such as lipid secretion to often invite dry skin. Therefore, there is a demand for a skin preparation for external use to prevent dry skin and provide an excellent moisturizing effect.

Various active compounds having a moisturizing effect have been provided, which are mainly based on water-soluble polyols. Some of them including propylene glycols have already been commercialized. However, many of commercialized moisturizing compounds are associated with uncomfortable feel during application or insufficient moisturizing effect, so that there is still a demand for the development of a new moisturizing compound.

An alternative moisturizing compound is sodium hyaluronate, which draws special interest as a valuable compound because of high hydration effect. However, aqueous solutions of sodium hyaluronate have a disadvantage in stability, which is high at neutral pH range but lowered in acidic solutions or salt solutions. This leads to the problem that the moisturizing effect cannot be effectively produced under some storage conditions or application conditions during use as cosmetics or the like, and there is a need for a solution thereto.

In view of these problems of the prior art, our studies were devoted to provide a material that stably exists even in low-pH solutions or salt solutions and has excellent emulsifiability and hydration effect. Thus, an object of the present invention is to provide a compound that can be widely used as cosmetic and pharmaceutical products because of excellent viscosity stability, emulsifiability, hydration power and moisturizing effect.

SUMMARY OF THE INVENTION

As a result of careful studies to attain the above object, we accomplished the present invention on the basis of the finding that propylene glycol hyaluronate esters satisfying specific conditions have excellent properties.

Accordingly, the present invention provides propylene glycol hyaluronate esters having an esterification degree of 10–90%, preferably 20–80%, more preferably 30–70%, even more preferably 40–60%. The present invention also provides propylene glycol hyaluronate esters having a limiting viscosity of 3–35 dL/g, preferably 11–27 dL/g, more preferably 14–20 dL/g. Especially preferred propylene glycol hyaluronate esters of the present invention are compounds having an esterification degree of 40–60% and a limiting viscosity of 14–20 dL/g.

Propylene glycol hyaluronate esters of the present invention are preferably combined with imidazoline-based amphoteric surfactants such as 2-lauryl-N-carboxymethyl-N-hydroxyethyl imidazolinium betaine and 2-alkyl-N-carboxymethyl-N-hydroxyethyl imidazolinium betaine.

The present invention also provides skin preparations for external use containing said propylene glycol hyaluronate esters. Skin preparations for external use according to the present invention are useful as moisturizers and emulsifiers, especially as emulsifiers for low-pH systems, emulsifiers for cation-containing systems and high-hydration emulsifiers.

Numerical ranges used herein include both limits.

DETAILED DESCRIPTION OF THE INVENTION

Propylene glycol hyaluronate esters and skin preparations for external use according to the present invention will now be explained in detail.

Propylene glycol hyaluronate esters of the present invention are compounds having an esterification degree of 10–90% or a limiting viscosity of 3–35 dL/g. The esterification degree is preferably 20–80%, more preferably 30–70%, even more preferably 40–60%. The limiting viscosity is preferably 11–27 dL/g, more preferably 13–23 dL/g, even more preferably 14–20 dL/g.

Propylene glycol hyaluronate esters of the present invention are preferably compounds having an esterification degree of 10–90% and a limiting viscosity of 3–35 dL/g, more preferably compounds having an esterification degree of 20–80% and a limiting viscosity of 11–27 dL/g, even more preferably compounds having an esterification degree of 30–70% and a limiting viscosity of 13–23 dL/g, most preferably compounds having an esterification degree of 40–60% and a limiting viscosity of 14–20 dL/g.

As used herein, the "esterification degree" means the proportion of esterified carboxylates among those forming hyaluronic acid. The limiting viscosity of propylene glycol hyaluronate esters can be determined according to the method of Laurent et al. (T. C. Laurent et al. Biochem. Biophys. Acta, 42(1960)476–485).

The type and structure of the hyaluronic acid moiety forming propylene glycol hyaluronate esters of the present invention are not specifically limited. The molecular weight of hyaluronic acid, which is a polysaccharide having repeating units of a disaccharide consisting of D-glucuronic acid and N-acetyl-D-glucosamine, is not specifically limited so far as the limiting viscosity of the resulting propylene glycol esters falls within said range. Hyaluronic acid used herein may be synthesized or purified from natural origins by known means. Substituents on D-glucuronic acid and N-acetyl-D-glucosamine forming ihyaluronic acid may be partially derivatized unless the effects of the present invention are excessively hindered. For example, hydroxyl groups may be substituted by alkoxy or other groups. These substitutions can be appropriately carried out within the scope of those skilled in the art.

In propylene glycol hyaluronate esters of the present invention, acid moieties and ester moieties may be localized in their molecules or may be widely distributed. However, those having two or more molecules of hyaluronic acid crosslinked via propylene glycol are excluded.

Processes for preparing propylene glycol hyaluronate esters of the present invention are not specifically limited. An especially preferred process involves reacting a mixture of hyaluronic acid and sodium hyaluronate with propylene oxide. More specifically, sodium hyaluronate is first partially converted into hyaluronic acid in the presence of a hydrochloric acid/ethanol solution or the like and then the reaction mixture is washed with ethanol to give a mixture of hyaluronic acid and sodium hyaluronate. Then, this mixture is esterified with a solution of propylene oxide in ethanol. Preferably, the temperature of the esterification reaction here is 50–80° C. and the reaction time is about 1–10 hours. After reaction, the reaction product may be washed with ethanol, neutralized with a solution of sodium acetate in ethanol, washed with ethanol again, and then dried. According to this process, a propylene glycol hyaluronate ester having the intended effects of the present invention can be efficiently prepared.

Propylene glycol hyaluronate esters of the present invention are quite useful as ingredients of skin preparations for external use. Propylene glycol hyaluronate esters of the present invention are compounds showing excellent viscosity stability in low-pH systems and cation-containing systems and also showing high emulsifiability, hydration power and moisturizing effect. Thus, skin preparations for external use containing a propylene glycol hyaluronate ester of the present invention are useful as moisturizers, emulsifiers for low-pH systems, emulsifiers for cation-containing systems and high-hydration emulsifiers.

Skin preparations for external use according to the present invention were found to have especially high stability and excellent moisturizing effect so that they provide appropriate moisture to the surface of the skin to keep smoothness. That is, skin preparations for external use according to the present invention can keep moisture in the skin for a long period. Such an effect of the present invention is especially remarkable in propylene glycol hyaluronate esters satisfying the conditions described above. It could not be expected that such compounds are much effective than similar hyaluronate esters departing from the conditions described above.

For example, skin preparations for external use according to the present invention can be used as cosmetic or pharmaceutical products, such as toilet soaps, shampoos, face washes, rinses, eye creams, eye shadows, creams and/or emulsions, lotions, perfumes, face powders, cosmetic oils, cosmetic products for hair and scalp, hair dyes, solid perfumes, powders, packs, shaving creams, shaving lotions, suntan oils, sunscreen oils, suntan lotions, sunscreen lotions, suntan creams, sunscreen creams, foundations, powder perfumes, cheek colors, mascaras, eyebrow colors, nail creams, nail enamels, nail enamel removers, hair washes, bath cosmetics, lip colors, lip creams, eyeliners, dentrifrices, deodorant products, eaux de cologne, hair growers, etc. Skin preparations for external use according to the present invention may also be used as ointments or fomentations.

Skin preparations for external use according to the present invention may also contain various ingredients other than said propylene glycol hyaluronate esters depending on the purpose of use such as improvement of emollient effect, improvement of feel of use, moderation of dehydration after use, improvement of solubility, improvement of emulsifiability, improvement of emulsification stability, improvement of compatibility with oily ingredients, moderation of feel of stretch after use, improvement of skin fit, improvement of spreadability on the skin, moderation of greasiness, prevention of dry skin, enhancement of skin-improving effect, improvement of skin-protecting effect, keratin improvement, normalization of epidermal keratinization (prevention of parakeratosis, prevention of acanthosis and inhibition of disorder of epidermal lipid metabolism via promoted turnover of the skin), moderation of xeroderma such as senile xeroderma, improvement of dry skin conditions such as crack or desquamation, inhibition of the formation of wrinkles, removal of wrinkles, wound healing, prevention and improvement of pigmentation, antiaging, moderation of dandruff or itch, moderation of loss of hair, prevention and treatment of scalp diseases, improvement of setting, improvement of softness, improvement of elasticity, glossing, suppression of melanogenesis, prevention of sunburn, etc.

Depending on the purpose of use, skin preparations for external use according to the present invention may appropriately contain other ingredients such as fats and oils, phospholipids, UV absorbers, IR absorbers, emulsifiers, surfactants, preservatives, antifungal agents, antioxidants, whitening agents, vitamins, amino acids, hormones, peptides, bioactive plant extracts, fluorescent materials, pigments, dyes, perfumes, scrubbing agents, sequestrants, binders, fillers, thickeners, sugars, nutrient ingredients, pH modulators, chelating agents, antibacterials, keratin improvers, keratolytic agents, antibiotics, skin penetration enhancers, blood circulation promoters, antiphlogistics, cytotonic agents, antiinflammatory agents, analgesics, skin softeners, emollients, woundhealing agents, metabolism enhancers, etc. Additional moisturizing ingredients other than propylene glycol hyaluronate esters of the present invention may also be contained.

Suitable fats and oils for use in skin preparations for external use according to the present invention include fatty acids such as oleic acid, behenic acid, isostearic acid, lauric acid, myristic acid, palmitic acid, stearic acid, behenic acid, linolic acid, γ-linolenic acid, columbic acid, eicosa-(n-6,9, 13)-trienoic acid, arachidonic acid, α-linolenic acid, tymnodonic acid, hexaenoic acid; ester oils such as pentaerythritol-tetra-2-ethyl hexanoate, isopropyl myristate, butyl stearate, hexyl laurate, octyldodecyl myristate, diisopropyl adipate, diisopropyl sebacate; waxes such as beeswax, spermaceti, lanolin, carnauba wax, candelilla wax, vaseline; animal and plant oils such as mink oil, olive oil, castor oil, cacao butter, palm oil, cod liver oil, beef tallow, butter fat, evening primrose oil, rice bran oil, squalane; mineral oils such as hydrocarbon oils, liquid paraffin; silicone oils such as methyl phenyl silicone, dimethyl silicone; higher alcohols such as lauryl alcohol, stearyl alcohol, oleyl alcohol, cetyl alcohol, 2-octyl dodecanol, 2-decyl tetradecanol and derivatives thereof. Suitable organic acids include α-hydroxy acid, hydroxycarboxylic acid, dicarboxylic acid, glycyrrhizic acid, glycyrrhetic acid, mevalonic acid (mevalolactone).

Suitable phospholipids for use in skin preparations for external use according to the present invention include monoacylester-type glycerophospholipids and diacylester-type glycerophospholipids. Specific examples include lysophosphatidylcholine, lysophosphatidylethanolamine, lysophosphatidylserine, lysophosphatidylinositol, phosphatidylcholine, phosphatidylethanolamine, phosphatidylinositol, phosphatidylserine, phosphatidylglycerol, phosphatidic acid, sphingomyelin. Naturally derived lecithins such as yolk and hydrogenates of the compounds mentioned above may also be used.

Suitable UV absorbers for use in skin preparations for external use according to the present invention include oxybenzone (2-hydroxy-4-methoxybenzophenone), oxybenzonesulfonic acid, oxybenzonesulfonic acid (trihydrate), guaiazulene, ethylene glycol salicylate, octyl salicylate, dipropylene glycol salicylate, phenyl salicylate, homomenthyl salicylate, methyl salicylate, methyl diisopropylcinnamate, cinoxate (2-ethoxyethyl p-methoxycinnamate), glyceryl mono-2-ethylhexyl-di-p-methoxycinnamate, 2,2'-dihydroxy-4- methoxybenzophenone, sodium 2,2'-dihydroxy-4-methoxybenzophenone-5,5'-disulfonate, 2,4-dihydroxybenzophenone, 2,3,4,4'-tetrahydroxybenzophenone, p-aminobenzoic acid, ethyl p-aminobenzoate, glyceryl p-aminobenzoate, amyl p-dimethylaminobenzoate, 2-ethylhexyl p-dimethylaminobenzoate, p-hydroxyanisol, 2-ethylhexyl p-methoxycinnamate, isopropyl p-methoxycinnamate, diisopropyl cinnamate ester, 2-(2-hydroxy-5-methylphenyl) benzotriazole, sodium 2-hydroxy-4-methoxybenzophenone-5-sulfonate, 4-tert-butyl-4'-methoxybenzoylmethane, 2-ethylhexyl salicylate, glyceryl p-monobenzoate, methyl orthoaminobenzoate, 2-hydroxy-4-methoxybenzophenone, amyl p-dimethylaminobenzoate, 2-phenylbenzimidazol-5-sulfonic acid, 2-hydroxy-4-methoxybenzophenone-5-sulfonic acid, dicaproyl trioleate, 2-ethoxyethyl p-methoxycinnamate, butylmethoxy-dibenzoylmethane, glyceryl mono-2-ethylhexanoyl-di-p-methoxybenzophenone, 2-ethylhexyl-2-cyano-3,3'-diphenylacrylate, 2,2'-dihydroxy-4-methoxybenzophenone, ethyl 4-bishydroxypropyl aminobenzoate.

Suitable emulsifiers and surfactants for use in skin preparations for external use according to the present include nonionic surfactants, anionic surfactants, cationic surfactants and amphoteric surfactants.

Examples of nonionic surfactants include sorbitan esters such as sorbitan monolaurate, sorbitan monooleate, sorbitan monoisostearate; polyoxyethylene sorbitan esters such as polyoxyethylene sorbitan monoisostearate, polyoxyethylene sorbitan monolaurate, polyoxyethylene sorbitan monooleate; glycerol ethers such as glycerol monoisostearate, glycerol monomyristate; polyoxyethylene glycerol ethers such as polyoxyethylene glycerol monoisostearate, polyoxyethylene glycerol monomyristate; polyglycerin fatty acid esters such as diglyceryl monostearate, decaglyceryl decaisostearate, diglyceryl diisostearate; glycerin fatty acid esters such as glyceryl monocaprate, glyceryl monolaurate, glycerylmonomyristate, glycerylmonopalminate, glycerylmonooleate, glyceryl monostearate, glyceryl monolinoleate, glyceryl monoisostearate, glyceryl monodilinoleate, glyceryl monodicaprate; polyoxyethylene glycerin fatty acid esters such as polyoxyethylene glyceryl monomyristate, polyoxyethylene glyceryl monooleate, polyoxyethylene glyceryl monostearate; polyoxyethylene branched alkyl ethers such as polyoxyethylene octyldodecyl alcohol, polyoxyethylene-2-decyltetradecyl alcohol; polyoxyethylene alkyl ethers such as polyoxyethylene oleyl alcohol ether, polyoxyethylene cetyl alcohol ether; polyoxyethylene hydrogenated castor oil fatty acid esters such as polyoxyethylene hydrogenated castor oil, polyoxyethylene dihydrocholesterol ether, polyoxyethylene hydrogenated castor oil isostearate; polyoxyethylene alkyl aryl ethers such as polyoxyethylene octyl phenol ether.

Examples of anionic surfactants include salts of higher fatty acids such as oleic acid, stearic acid, isostearic acid, palmitic acid, myristic acid, behenic acid, for example, diethanolamine salts, triethanolamine salts, amino acid salts, potassium salts, sodium salts, ether carboxylic acid alkali salts, N-acylamino acid salts, N-acyl sarcosinates, higher alkyl sulfonates. Examples of cationic or amphoteric surfactants include alkyl quaternary ammonium salts, polyamines and alkyl amine salts.

Skin preparations for external use according to the present invention are preferably used in combination with amphoteric surfactants, among which imidazoline-based amphoteric surfactants are especially preferred. As used herein, the "imidazoline-based amphoteric surfactants" refer to amphoteric surfactants containing an imidazoline ring in their molecules and amphoteric surfactants having an opened imidazoline ring. Examples of imidazoline-based amphoteric surfactants include 2-alkyl-N-carboxymethyl-N-hydroxyethyl imidazolinium betaine, sodium N-cocoyl-N'-carboxylethyl-N'-hydroxyethyl ethylenediamine, disodium N-cocoyl-N'-carboxymethoxyethyl-N'-carboxymethyl ethylenediamine and disodium N-cocoyl-N'-carboxymethoxyethyl-N'-carboxymethyl ethylenediamine lauryl sulfate, among which 2-alkyl-N-carboxymethyl-N-hydroxyethyl imidazolinium betaine is especially preferred. These imidazoline-based amphoteric surfactants are commercially available under trade names such as Amphitol 20YB from Kao Corporation; ENAGICOL C-40H, CNS from Lion Corporation; LEBON 105, CIB from Sanyo Chemical Industries, Ltd.; Obazoline 662Y, 662N, 662SF, CS-65 from Toho Chemical Industry Co., Ltd; Miranol C2M-NP, Miracare 2MCA/P, Miranol ULTRAC-32 from Rhodia Nikka; Rewoteric AM2CNM, AMC from Goldschmidt AG; among which Amphitol 20YB, Obazoline 662N and Miranol ULTRAC-32 can be preferably used.

Imidazoline-based amphoteric surfactants are preferably used in the amount of 0.01–50 parts by weight, more preferably 1–30 parts by weight, even more preferably 3–5 parts by weight per part by weight of propylene glycol hyaluronate esters of the present invention. Compositions containing a propylene glycol hyaluronate ester of the present invention and an imidazoline-based amphoteric surfactant are characterized by less change in viscosity during storage because of their high stability. Especially, propylene glycol hyaluronate esters having an esterification degree of 40–60% provide higher stability as compared with lower esters.

Suitable powders for use in skin preparations for external use according to the present invention include talc, kaolin, fuller earth, gum, starch, silica, silicic acid, aluminium silicate hydrate, chemically modified aluminium magnesium silicate, sodium polyacrylate, tetraalkyl aryl ammonium smectite, trialkyl aryl ammonium smectite, ethylene glycol monostearate, sodium carboxymethylcellulose, carboxyvinyl polymers, chalk, gummy matters, ethylene glycol monostearate, ethylene glycol distearate, etc.

Suitable polyols for use in skin preparations for external use according to the present invention include glycerin, polyglycerins (such as diglycerin, triglycerin, tetraglycerin), ethylene glycol, propylene glycol, 1,3-butylene glycol, 1,4-butylene glycol, dipropylene glycol, polyethylene glycol, sorbitol, erythritol, maltotriose, threitol, sucrose, glucose, maltose, multitose, fructose, xylitose.

Other materials suitable for use in skin preparations for external use according to the present invention include vitamins such as vitamin A, vitamin $B_1$, vitamin $B_2$, vitamin $B_6$, vitamin $B_{12}$, vitamin C, vitamin D, vitamin E, vitamin K; amino acids such as proline, leucine, isoleucine, alanine, threonine, lysine, cysteine, arginine; hormones such as estrogen, pregnenolone, adrenocortical hormone; peptides such as keratin, collagen, elastin; sugars as listed above for polyols; inorganic salts such as sodium chloride, sodium hydrogencarbonate, sodium carbonate, borax, sodium sulfate, sodium sulfide, sodium thiosulfate, sodium sesquicarbonate, magnesium oxide, calcium carbonate, magnesium carbonate, potassium chloride, potassium sulfide; *Streptococcus themophilus* cultures; sterols such as cholesterol, provitamin $D_3$, campesterol, stigmastanol, stigmasterol, 5-dihydrocholesterol, α-spinastenol, cholesterol fatty acid esters; sphingosines such as sphingosine, dihydrosphingosine, phytosphingosine, dehydrosphingosine, dehydrophytosphingosine, sphingadienine; ceramides; pseudoceramides; saponins; chitin derivatives; oligosaccharides such as maltose, xylobiose, isomaltose, lactose, sucrose, raffinose, maltotriose, xylotriose, maltotetraose, xylotetraose, maltopentaose, xylopentaose, maltohexaose, xylohexaose, maltoheptaose, xyloheptaose; acid mucopolysaccharides such as hyaluronic acid, chondroitih sulfate, dermatan sulfate, heparin, heparan sulfate; yeast extracts, etc.

Skin preparations for external use according to the present invention may further contain thickeners such as carboxyvinyl polymers, carboxymethylcellulose, polyvinyl alcohol, xanthan gum, carrageenan, alginates, propylene glycol alginate esters, gelatin; electrolytes such as sodium chloride; whitening agents such as arbutin, allantoin, vitamin E derivatives, glycyrrhizin, magnesium ascorbyl phosphate, kojic acid, pantothenic acid derivatives, placenta extract, coix seed extract, green tee, kudzu root, mulberry root, glycyrrhiza, scutellaria root, aloe, orange peel, chamomile, *Ganoderma lucidum*; skin protective agents such as retinol, retinol esters, retinoic acid; skin softeners such as stearyl alcohol, glyceryl monoricinoleate, mink oil, cetyl alcohol, stearic acid, coconut oil, castor oil, isostearic acid; emollients such as stearyl alcohol, glycerin monoricinoleate, glycerin monostearate, cetyl alcohol; skin penetration enhancers such as 2-methylpropane-2-ol, 2-propanol, ethyl 2-hydroxypropionate, 2,5-hexanediol, acetone, tetrahydrofuran; bioactive plant extracts such as aloe, arnica, glycyrrhiza, sage and swertia herb extracts; preservatives such as p-hydroxybenzoate esters, sodium benzoate, urea, methylparaben, ethylparaben, propylparaben, butylparaben; antiinflammatory agents such as salicylic acid; antibiotics such as triclosan; antioxidants such as α-tocopherol, butylhydroxytoluene; buffers such as triethanolamine or a combination of sodium hydroxide and lactic acid; keratolytic agents such as lactic acid, glycolic acid, malic acid, tartaric acid, citric acid; scrubbing agents such as polyethylene powder; pigments such as calcium, barium or aluminium lake, iron oxide, titanium dioxide, mica, etc.

Skin preparations for external use according to the present invention may also contain other materials depending on the purpose of use. The amount of each ingredient to be added and the method for adding it can be determined by those skilled in the art.

The following examples and test examples further illustrate the present invention. The materials, reagents, proportions, procedures or the like shown in the following examples can be appropriately changed without departing from the spirit of the present invention. Therefore, the scope of the present invention is not limited to the embodiments shown below.

EXAMPLES

Example 1

Preparation of Propylene Glycol Hyaluronate Esters

Sodium hyaluronate (300 g; hyaluronate FCH-200 available from Kibun Food Chemifa Co., Ltd.) was mixed with a mixed solution of 29.7 L of ethanol and 60 mL of hydrochloric acid and the mixture was stirred at room temperature for 30 minutes and then washed with ethanol/water (9:1) to give a mixture of hyaluronic acid and sodium hyaluronate.

Then, 100 g (dry weight) of this mixture was mixed with 104 mL of a solution of 6.2 equivalents of propylene oxide in ethanol/water (8:2) for esterification at 50° C. for 4 hours, followed by hyaluronate conversion as described above and further esterification at 50° C. for 8 hours. After reaction, the reaction product was washed with ethanol/water (9:1), neutralized with a solution of 1.5 equivalents of sodium acetate in ethanol/water (9:1), washed again with ethanol/water (9:1) and dried under reduced pressure at 40° C. for 2 hours to give a propylene glycol hyaluronate ester having an esterification degree of 47.6% and a limiting viscosity of 7.3 dL/g.

A plurality of propylene glycol hyaluronate esters having varying esterification degrees and limiting viscosities were prepared by the procedure described above.

Test Example 1

Stability Test at Low pH Range

Each sample was dissolved in a citrate buffer (0.2% aqueous paraben) at a sample concentration of 0.2% and stored at 50° C. for 14 days, after which viscosity change was determined at pH 3, pH 4 and pH 5. The table below shows the number of days before viscosity retention declined below 30%. Sodium hyaluronate used in the following test examples was FCH-120 available from Kibun Food Chemifa Co., Ltd. The abbreviations ED8.6 to ED90.8 refer to propylene glycol hyaluronate esters with the indices indicating esterification degrees. Viscosity was measured at 20° C. on a Brookfield rotational viscometer (Tokyo Keiki).

TABLE 1

|  | pH 3 | pH 4 | pH 5 |
| --- | --- | --- | --- |
| FCH-120 | 1 | 1 | 4 |
| ED8.6 | 1 | 4 | 8 |
| ED11.0 | 4 | 4 | 8 |
| ED26.5 | >14 | >14 | >14 |
| ED34.4 | >14 | >14 | >14 |
| ED51.2 | >14 | >14 | >14 |
| ED90.8 | >14 | >14 | >14 |

The results in the table above demonstrate that propylene glycol hyaluronate esters having an esterification degree of more than about 20% exhibit high stability in low-pH systems.

Test Example 2

Stability Test in the Presence of Cations

Each sample was added to an aqueous solution of NaCl, $CaCl_2$ or $MgCl_2$ (1.0 mol/L) at a sample concentration of 0.5% and the viscosity retention was determined after 30 minutes. The table below shows the results of evaluation in which "x" means viscosity retention of less than 20%, "Δ" means 20–30%, "○" means 30–40% and "⊙" means more than 40%. FCH-SU refers to a low molecular weight sodium hyaluronate available from Kibun Food Chemifa Co., Ltd.

TABLE 2

|  | NaCl | $CaCl_2$ | $MgCl_2$ |
| --- | --- | --- | --- |
| FCH-120 | Δ | x | x |
| FCH-SU | ○ | ○ | ○ |
| ED8.6 | ⊙ | ○ | ○ |
| ED11.0 | Δ | Δ | Δ |
| ED34.4 | ○ | ○ | ○ |
| ED51.2 | ⊙ | ⊙ | ⊙ |
| ED75.4 | ⊙ | ⊙ | ⊙ |

The results in the table above demonstrate that propylene glycol hyaluronate esters having an esterification degree of more than about 20% exhibit high stability in the presence of cations. Especially, propylene glycol hyaluronate esters having an esterification degree of more than 40% were shown to have high stability in the presence of cations.

Test Example 3
Stability Test in the Presence of Amphoteric Surfactants

Aqueous solutions of each of Amphitol 20YB available from Kao Corporation, Miranol ULTRAC-32 available from Nikko Chemicals Co., Ltd. and Obazoline 662N available from Toho Chemical Industry Co. were prepared at 3 different concentrations of 1.0%, 1.5% and 2.5%. Each sample was added to each aqueous amphoteric surfactant solution at a sample concentration of 0.5% and adjusted to pH 3 with hydrochloric acid. The viscosity retention was determined after storage at 50° C. for 30 days. The table below shows the results of evaluation based on the number of days before viscosity retention declined below 20% in which "x" means within one day, "△" means within 4 days, "○" means within 30 days and "⊙" means over 30 days. Samples used in this test example had a limiting viscosity of 18.0–19.0 dL/g.

TABLE 3

|  | 20YB | | | ULTRAC-32 | | | 662N | | |
| --- | --- | --- | --- | --- | --- | --- | --- | --- | --- |
|  | 1.0 | 1.5 | 2.5 | 1.0 | 1.5 | 2.5 | 1.0 | 1.5 | 2.5 |
| FCH-80 | X | X | X | X | X | △ | X | X | X |
| ED18.9 | ○ | ○ | ⊙ | △ | △ | ○ | △ | X | X |
| ED42.2 | ⊙ | ⊙ | ⊙ | ⊙ | ⊙ | ⊙ | ○ | ○ | ⊙ |
| ED59.4 | ⊙ | ⊙ | ⊙ | ⊙ | ⊙ | ⊙ | ⊙ | ⊙ | ⊙ |

The results in the table above demonstrate that compositions containing a propylene glycol hyaluronate ester of the present invention and an imidazoline-based amphoteric surfactant exhibit high stability. Especially, propylene glycol hyaluronate esters having an esterification degree of more than 40% were shown to have high stability in the presence of imidazoline-based amphoteric surfactants.

Test Example 4
Emulsifiability Test

An aqueous solution of each sample was added to a 1:1 mixed solution of distilled water and squalane at a sample concentration of 0.5% or 1.0%. Then, the mixed solution was heated to 70° C. and stirred with a hand homogenizer at 10000 rpm for 2 minutes, and allowed to cool down to room temperature to observe separation state after 4 hours. Emulsification stability was evaluated from the extent of separation according to 4 ratings of ⊙, ○, △, x.

TABLE 4

|  | Sample concentration | |
| --- | --- | --- |
|  | 0.5% | 1.0% |
| FCH-120 | x | x |
| ED8.6 | x | x |
| ED26.5 | ○ | ⊙ |
| ED27.2 | ⊙ | ⊙ |
| ED34.4 | ⊙ | ⊙ |
| ED54.4 | ⊙ | ⊙ |
| ED61.0 | ○ | ⊙ |
| ED75.4 | ○ | ⊙ |
| ED81.7 | ○ | ○ |

The results in the table above demonstrate that propylene glycol hyaluronate esters having an esterification degree of more than about 20% exhibit high emulsification stability.

The same emulsification stability test was performed on ED26.5 and higher esters with varying limiting viscosities to show that high stability is obtained at a limiting viscosity of 3–35 dL/g, preferably 6–35 dL/g, more preferably 11–27 dL/g, even more preferably 14–20 dL/g.

Test Example 5
Emulsifiability Test at Low pH Range

An aqueous solution of each sample at a sample concentration of 0.1% was prepared and adjusted to pH 3–6 with hydrochloric acid and sodium hydroxide. To 10 g of this aqueous solution was added 10 g of squalane, and the mixed solution was heated at 70° C. for 5 minutes, then homogenized at 5000 rpm for 2 minutes and then allowed to stand at room temperature and evaluated for emulsification stability.

A series of 6 propylene glycol hyaluronate esters having esterification degrees of 13.5–59.4% and limiting viscosities of 16.55–19.0 dL/g according to the present invention were tested in comparison with a control FCH-80 to show that all of the samples according to the present invention have significantly higher emulsification stability than the control sample.

Another series of 3 propylene glycol hyaluronate esters having esterification degrees of 59.4–61.1% and limiting viscosities of 7.88–18.1 dL/g according to the present invention were tested in comparison with 3 control samples FCH-SU, 60 and 80 to show that all of the samples according to the present invention have significantly higher emulsification stability than the control samples.

Thus, propylene glycol hyaluronate esters of the present invention were shown to have high emulsification stability at pH range of 3–6.

Test Example 6
Hydration Test

A filter paper was immersed 1 cm from one end in 50 mL each of aqueous solutions of each sample having concentrations of 0.05%, 0.1%, 0.2% and 0.5%, and allowed to stand as such for 30 minutes and then removed from the aqueous solution to measure the distance of water moved from the water level. The distance becomes longer as hydration power increases. The hydration power of each sample was evaluated according to 4 ratings ⊙, ○, △, x.

TABLE 5

|  | Hydration power |
| --- | --- |
| FCH-SY | △ |
| ED11.0 | △ |
| ED34.4 | ○ |
| ED51.2 | ⊙ |
| ED81.7 | ⊙ |

The results in the table above demonstrate that propylene glycol hyaluronate esters having an esterification degree of more than about 20% exhibit high hydration power.

Test Example 7
Hydration Test at Low pH Range

An aqueous solution of each sample at a sample concentration of 0.5% or 1.0% was prepared and adjusted to pH 3–6 with hydrochloric acid and sodium hydroxide. A vial having a diameter of 3 cm was charged with this aqueous solution and covered with a filter paper, and then placed in an incubator at 30° C. Change of the weight of the aqueous solution in each vial was measured over time and the amount of moisture evaporated off was determined to evaluate hydration.

Two propylene glycol hyaluronate esters having esterification degrees of 13.5–59.4% and limiting viscosities of 16.9–18.1 dL/g according to the present invention were tested in comparison with a control FCH-80 to show that both samples according to the present invention have significantly higher hydration power than the control sample.

Thus, propylene glycol hyaluronate esters of the present invention were shown to have high hydration power at pH range of 3–6.

Example 2
Preparation of Beauty Lotions

Various ingredients described in the table below were mixed at room temperature and thoroughly stirred to prepare beauty lotions. In the following examples, the "active ingredient" refers to a propylene glycol hyaluronate ester having an esterification degree of 10–90% and a limiting viscosity of 3–35 dL/g.

TABLE 6

| Ingredient | Part by weight |
|---|---|
| Active ingredient | 1.0 |
| Methylparaben | 0.1 |
| Polyoxyethylene hydrogenated castor oil | 1.2 |
| Polyoxyethylene sorbitan oleate | 0.4 |
| Ethanol | 5.3 |
| Purified water | 92.0 |

Example 3
Preparation of Powder Foundations

Various ingredients described in the table below were mixed at room temperature and thoroughly stirred to prepare powder foundations.

TABLE 7

| Ingredient | Part by weight |
|---|---|
| Active ingredient | 1.0 |
| Mica | 37.8 |
| Talc | 20.0 |
| Titanium dioxide | 12.0 |
| Kaolin | 5.0 |
| Iron oxide | 3.5 |
| Nylon powder | 8.0 |
| Octyldodecyl myristate | 2.0 |
| Neopentylglycol diisooctanoate | 2.0 |
| Sorbitan monooleate | 0.5 |
| Zinc stearate | 1.0 |
| Red oxide | 1.0 |
| Squalane | 6.0 |
| Preservative | 0.1 |
| Antioxidant | 0.1 |

Example 4
Preparation of Whitening Powders

Various ingredients described in the table below were mixed and pulverized at room temperature to prepare whitening powders.

TABLE 8

| Ingredient | Part by weight |
|---|---|
| Active ingredient | 20.0 |
| Sucrose | 50.0 |
| Polyethylene glycol | 10.0 |
| Silica | 4.5 |

TABLE 8-continued

| Ingredient | Part by weight |
|---|---|
| Vitamin C | 5.0 |
| Vitamin C dipalmitate | 10.0 |
| Dye | 0.5 |

Example 5
Preparation of Emollient Creams

After 1,3-butylene glycol and purified water described in the table below were mixed and heated to 70° C., a mixture of the remaining ingredients molten by heating was added and the emulsified particles were homogenized and cooled to prepare emollient creams.

TABLE 9

| Ingredient | Part by weight |
|---|---|
| Active ingredient | 5.0 |
| Stearyl alcohol | 6.0 |
| Stearic acid | 2.0 |
| Hydrogenated lanolin | 4.0 |
| Squalane | 9.0 |
| Octyl dodecanol | 10.0 |
| POE (25) cetyl alcohol ether | 3.0 |
| Glycerin monostearate | 2.0 |
| 1,3-Butylene glycol | 10.0 |
| Dye | 0.5 |
| Preservative | 0.1 |
| Antioxidant | 0.1 |
| Purified water | 48.3 |

Example 6
Preparation of Cleansing Foams

Stearic acid, palmitic acid, myristic acid, lauric acid, coconut oil and preservative described in the table below were molten by heating and kept at 70° C. and a mixture of potassium hydroxide and purified water was added with stirring. Then, the remaining ingredients were added and the mixture was thoroughly stirred and then deaerated and cooled to prepare cleansing foams.

TABLE 10

| Ingredient | Part by weight |
|---|---|
| Active ingredient | 4.5 |
| Stearic acid | 10.0 |
| Palmitic acid | 10.0 |
| Myristic acid | 12.0 |
| Lauric acid | 4.0 |
| Coconut oil | 2.0 |
| Potassium hydroxide | 6.0 |
| Glycerol monostearate ester | 2.0 |
| POE (25) sorbitan monostearate | 2.0 |
| Dye | 0.5 |
| Preservative | 0.1 |
| Chelating agent | 0.2 |
| Purified water | 46.7 |

Example 7
Preparation of Packs

Titanium oxide and talc described in the table below were thoroughly dispersed in purified water and then combined with sorbitol. The mixture was molten by heating to 70° C. and combined with the remaining ingredients and the mixture was thoroughly stirred and then deaerated and cooled to prepare packs.

TABLE 11

| Ingredient | Part by weight |
| --- | --- |
| Active ingredient | 4.5 |
| Polyvinyl acetate emulsion | 15.0 |
| Polyvinyl alcohol | 10.0 |
| Jojoba oil | 2.0 |
| Squalane | 2.0 |
| POE sorbitan monostearate ester | 1.0 |
| Titanium oxide | 5.0 |
| Talc | 10.0 |
| Sorbitol | 10.0 |
| Ethanol | 8.0 |
| Dye | 0.5 |
| Preservative | 0.2 |
| Purified water | 31.8 |

Example 8
Preparation of Lipsticks

Various ingredients described in the table below were heated to 70° C. and then mixed. The mixture was thoroughly stirred and cast and then rapidly cooled to prepare lipsticks.

TABLE 12

| Ingredient | Part by weight |
| --- | --- |
| Active ingredient | 2.0 |
| Castor oil | 25.0 |
| Cetyl 2-ethylhexanoate | 20.0 |
| Lanolin | 10.0 |
| Isopropyl myristate ester | 10.0 |
| Candelilla wax | 9.0 |
| Solid paraffin | 8.0 |
| Carnauba wax | 5.0 |
| Beeswax | 5.0 |
| Titanium dioxide | 5.0 |
| Dye | 1.0 |

Example 9
Preparation of Lip Creams

Active ingredient, stearic acid, stearyl alcohol and butyl stearate described in the table below were heated to 70° C. and then mixed and combined with a mixture of the remaining ingredients. The mixture was thoroughly stirred to prepare lip creams.

TABLE 13

| Ingredient | Part by weight |
| --- | --- |
| Active ingredient | 4.0 |
| Stearic acid | 14.0 |
| Stearyl alcohol | 8.0 |
| Butyl stearate | 10.0 |
| Propylene glycol | 10.0 |
| Glycerin monostearate | 4.0 |
| Potassium hydroxide | 1.0 |
| Antioxidant | 0.2 |
| Purified water | 48.8 |

Example 10
Preparation of Cheek Colors

Various ingredients except for perfume and liquid paraffin described in the table below were mixed at room temperature and then sprayed with perfume and liquid paraffin and pulverized. The mixture was compression molded to prepare cheek colors.

TABLE 14

| Ingredient | Part by weight |
| --- | --- |
| Active ingredient | 1.5 |
| Talc | 77.8 |
| Kaolin | 9.0 |
| Zinc myristate | 5.0 |
| Pigment | 3.0 |
| Liquid paraffin | 3.0 |
| Perfume | 0.5 |
| Preservative | 0.2 |

Example 11
Preparation of Eyeliners

Carbon black described in the table below was pulverized and then dispersed in purified water, and the remaining ingredients were mixed at room temperature to prepare eyeliners.

TABLE 15

| Ingredient | Part by weight |
| --- | --- |
| Active ingredient | 10.0 |
| Carbon black | 5.0 |
| Polyoxyethylene dodecyl ether | 2.0 |
| Dye | 0.5 |
| Preservative | 0.2 |
| Purified water | 82.3 |

Example 12
Preparation of Mascaras

Iron oxide, purified water and polyacrylate ester emulsion described in the table below were mixed at 70° C. and combined with a mixture of the remaining ingredients molten by heating to 70° C. The mixture was dispersed by emulsification to prepare mascaras.

TABLE 16

| Ingredient | Part by weight |
| --- | --- |
| Active ingredient | 4.5 |
| Iron oxide | 10.0 |
| Polyacrylate ester emulsion | 27.0 |
| Solid paraffin | 8.0 |
| Lanolin wax | 8.0 |
| Light isoparaffin | 28.0 |
| Sorbitan sesquioleate | 4.0 |
| Dye | 0.5 |
| Antioxidant | 0.1 |
| Preservative | 0.1 |
| Purified water | 9.8 |

Example 13
Preparation of Eyebrow Colors

Various ingredients except for powdery ingredients described in the table below were molten and mixed, and then combined with powdery ingredients. The mixture was kneaded and molded to prepare eyebrow colors.

TABLE 17

| Ingredient | Part by weight |
| --- | --- |
| Active ingredient | 1.0 |
| Iron oxide | 19.0 |
| Titanium oxide | 5.0 |

TABLE 17-continued

| Ingredient | Part by weight |
|---|---|
| Talc | 10.0 |
| Kaolin | 15.0 |
| Japan wax | 20.0 |
| Stearic acid | 10.0 |
| Beeswax | 5.0 |
| Hydrogenated castor oil | 5.0 |
| Vaseline | 4.0 |
| Lanolin | 3.0 |
| Liquid paraffin | 2.8 |
| Antioxidant | 0.1 |
| Preservative | 0.1 |

Example 14
Preparation of Hand Creams

Various ingredients described in the table below were mixed under heating at 70° C. and thoroughly stirred to prepare hand creams.

TABLE 18

| Ingredient | Part by weight |
|---|---|
| Active ingredient | 3.0 |
| Glycerin | 20.0 |
| Urea | 2.0 |
| Monoglyceride stearate | 2.5 |
| Vaseline | 6.0 |
| Liquid paraffin | 10.0 |
| Purified water | 56.5 |

Example 15
Preparation of Hair Shampoos

Various ingredients described in the table below were mixed under heating at 70° C. and thoroughly stirred to prepare hair shampoos.

TABLE 19

| Ingredient | Part by weight |
|---|---|
| Active ingredient | 5.0 |
| Glycerin | 1.0 |
| Sodium polyoxyethylene lauryl sulfate ester | 10.0 |
| Sodium lauryl sulfate ester | 6.0 |
| Coconut fatty acid diethanolamide | 3.0 |
| Sequestrant | 0.1 |
| pH modulator | 0.5 |
| Preservative | 0.2 |
| Purified water | 74.2 |

Example 16
Preparation of Hair Rinses

Various ingredients described in the table below were mixed under heating at 70° C. and thoroughly stirred to prepare hair rinses.

TABLE 20

| Ingredient | Part by weight |
|---|---|
| Active ingredient | 3.0 |
| Silicone oil | 2.8 |
| Liquid paraffin | 1.2 |
| Glycerin | 2.5 |
| Cetyl alcohol | 1.3 |

TABLE 20-continued

| Ingredient | Part by weight |
|---|---|
| Stearyl alcohol | 1.1 |
| Stearyltrimethylammonium chloride | 0.6 |
| Dye | 1.0 |
| Preservative | 0.2 |
| Purified water | 86.3 |

Example 17
Preparation of Hair Lotions

Various ingredients described in the table below were mixed at room temperature to prepare hair lotions.

TABLE 21

| Ingredient | Part by weight |
|---|---|
| Active ingredient | 1.0 |
| Polyoxypropylene butyl ether | 20.0 |
| Polyoxyethylene hydrogenated castor oil | 1.0 |
| Ethanol | 50.0 |
| Perfume | 0.5 |
| Purified water | 27.5 |

Example 18
Preparation of Bath Formulas

Various ingredients described in the table below were mixed at room temperature to prepare bath formulas.

TABLE 22

| Ingredient | Part by weight |
|---|---|
| Active ingredient | 10 |
| Sodium sulfate | 50 |
| Sodium hydrogencarbonate | 25 |
| Sodium chloride | 13 |
| Dye | 2 |

As apparent from the foregoing description, propylene glycol hyaluronate esters of the present invention are compounds showing excellent viscosity stability in low-pH systems and cation-containing systems and also showing high emulsifiability, hydration power and moisturizing effect. Therefore, skin preparations for external use according to the present invention are especially useful as moisturizers, emulsifiers for low-pH systems, emulsifiers for cation-containing systems and high-hydration emulsifiers.

What is claimed is:

1. An emulsification method comprising mixing a liquid containing water and a hydrophobic component with a propylene glycol hyaluronate ester having an esterification degree of 10–90% at a pH of 3–5.

2. The method of claim 1 wherein said liquid is a cation-containing liquid.

3. An emulsification method of claim 1 wherein said propylene glycol hyaluronate ester has a limiting viscosity of 3–35 dL/g.

4. The emulsification method of claim 1 wherein said pH is 3–4.

5. The emulsification method of claim 4 wherein said propylene glycol hyaluronate ester has a limiting viscosity of 11–27 dL/g.

6. The emulsification method of claim 4 wherein said propylene glycol hyaluronate ester has a limiting viscosity of 14–20 dL/g.

7. The emulsification method of claim 4 wherein said propylene glycol hyaluronate ester has an esterification degree of 20–80%.

8. The emulsification method of claim 4 wherein said propylene glycol hyaluronate ester has an esterification degree of 30–70%.

9. The emulsification method of claim 4 wherein said propylene glycol hyaluronate ester has an esterification degree of 40–60%.

10. The emulsification method of claim 1 wherein said pH is within the range of 3 to less than 5.

11. The emulsification method of claim 1 wherein said pH is within the range of 3 to about 4.

12. The emulsification method of claim 1 wherein said pH is about 3.

13. The emulsification method of claim 1 wherein said pH is about 4.

14. The emulsification method of claim 1 wherein said liquid containing water and propylene glycol hyaluronate ester further comprises a surfactant.

15. The emulsification method of claim 14 wherein said surfactant is an amphoteric surfactant.

16. The emulsification method of claim 1 wherein said hydrophobic component is an oily substance.

17. The emulsification method of claim 16 wherein said oily substance is a fat or oil adapted for use in skin preparations for external use.

* * * * *